United States Patent [19]

Fowlkes

[11] Patent Number: 5,175,369

[45] Date of Patent: Dec. 29, 1992

[54] SEPARATION OF METHOXYISOPROPYLAMINE FROM METHOXYISOPROPYLAMINE-WATER AZEOTROPE

[75] Inventor: Robert L. Fowlkes, Milton, Fla.

[73] Assignee: Air Products and Chemicals, Inc., Allentown, Pa.

[21] Appl. No.: 609,308

[22] Filed: Nov. 1, 1990

[51] Int. Cl.⁵ .................. C07C 209/84; C07C 209/16
[52] U.S. Cl. ........................................ 564/497; 203/14; 203/59; 564/474; 564/480; 564/499
[58] Field of Search ............... 564/497, 508, 499, 480, 564/474; 203/14, 59

[56] References Cited

U.S. PATENT DOCUMENTS

| | | | |
|---|---|---|---|
| 2,764,615 | 9/1956 | Data et al. | 564/508 |
| 3,033,864 | 5/1962 | Britton et al. | 260/250 |
| 3,433,788 | 3/1969 | Somekh et al. | 260/247 |
| 3,850,760 | 11/1974 | Lenel et al. | 564/499 |
| 4,868,335 | 9/1989 | Fowlkes et al. | 564/497 |

OTHER PUBLICATIONS

Komarov et al., "Isolation of Di-isopropylamine" *Soviet Inventions Illustrated* Jan. 1967, p. 512, abst. #180607.

Primary Examiner—Glennon H. Hollrah
Assistant Examiner—P. O'Sullivan
Attorney, Agent, or Firm—Russell L. Brewer; James C. Simmons; William F. Marsh

[57] ABSTRACT

This invention relates to a process for separating methoxyisopropylamine and particularly to an improvement in the process for the recovery of methoxyisopropylamine from the reaction of methoxyisopropanol with ammonia under amination conditions. In this process water is produced as a byproduct and in the separation process an azeotrope is formed which comprises about 14% water and 86% methoxyisopropylamine at atmospheric pressure. The process for enhancing separation of the azeotrope comprises contacting the azeotrope of methoxyisopropylamine and water with diisopropylamine in sufficient amount to form the azeotrope of water and diisopropylamine and separating the azeotrope from the other materials in a distillation column. The overheads in this column is charged to a decanter where water is removed as a bottoms phase and the diisopropylamine as the upper phase and returned as reflux to the distillation volumn. The water free crude methoxyisopropylamine is then charged to another column and the methoxyisopropylamine recovered as an overhead.

3 Claims, 1 Drawing Sheet

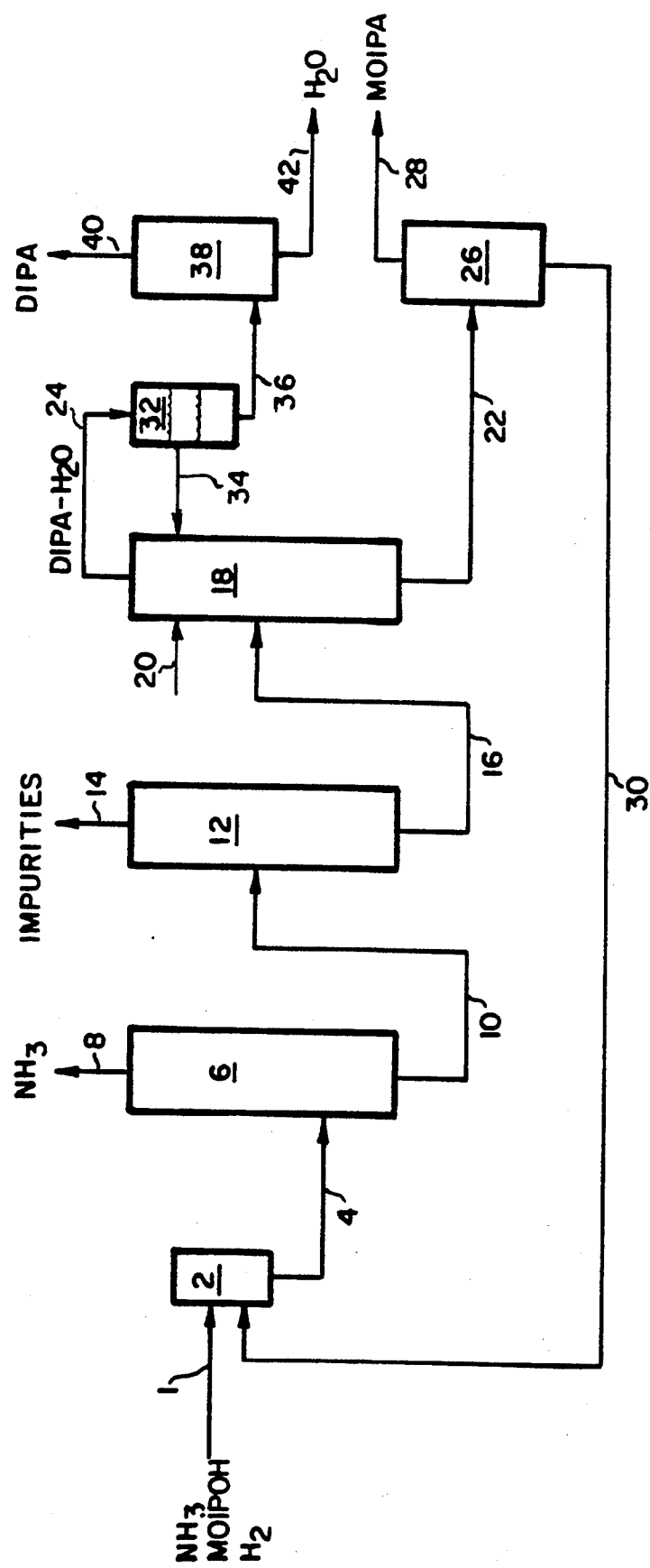

SEPARATION OF METHOXYISOPROPYLAMINE FROM METHOXYISOPROPYLAMINE-WATER AZEOTROPE

TECHNICAL FIELD

This invention related to the separation of methoxyisopropylamine from methoxyisopropylamine-water azeotrope.

BACKGROUND OF THE INVENTION

In the conventional manufacture of methoxyisopropylamine, methoxyisopropanol is contacted with ammonia in the presence of a catalyst under amination conditions to produce methoxyisopropylamine and by-product water. One of the problems in the recovery of the methoxyisopropylamine from the reaction mixture is that an azeotrope consisting of about 14% water and 86% methoxyisopropylamine is formed and thus creates a problem in the recovery of the methoxyisopropylamine from the reaction product. As is known, there are many procedures for breaking azeotropes. For example, one may adjust pressure or contact the azeotrope with another consolidation component which forms a lower boiling azeotrope with one of the compounds in the mixture. In the case of an organic in water azeotrope, one often may add a hydrocarbon as the codistillation agent to aid in the separation.

One of the problems associated with the methoxyisopropylamine-water azeotrope is that it is extremely difficult to produce a methoxyisopropylamine product which is essentially anhydrous, e.g., less than about 1% water. Any residual water in the methoxyisopropylamine tends to affect its usefulness as a reactant in many chemical reactions.

The following patents illustrate various approaches to the separation of amine-water azeotropes.

U.S. Pat. No. 4,868,335 discloses the recovery of mono-n-hexylamine from a mono-n-hexylamine-water azeotrope. To effect separation, the azeotrope is contacted with di-n-hexylamine or a mixture of di-n-hexylamine and tri-n-hexylamine. The di-n-hexylamine forms a lower boiling azeotrope with water and is removed by distillation. The organic phase then can be separated from the aqueous phase by decanting.

U.S. Pat. No. 3,433,788 discloses a process for recovering amines from aqueous solutions by solvent treatment and distillation. In particular the invention pertained to processes for the recovery of morpholine from aqueous solutions wherein the N-alkylmorpholines and some other amines form an azeotrope with water which could not be separated. Dewatering techniques involving the addition of sodium hydroxide were suggested, however, it was pointed out that the sodium hydroxide had to be recovered and that large amounts of water had to be removed by distillation. Ethyl ether was disclosed as being an extractant for morpholine but was unsatisfactory because of losses due to the high volatility of ethyl ether. The patentees suggested the utilization of an inert, water-immiscible, selective liquid organic solvent as an extractant. Specifically the extractants listed were organic vehicles which were inert to the amine and had a boiling point higher than the amine compound. Solvents included aliphatic alcohols, saturated aliphatic hydrocarbons, halogenated aliphatic hydrocarbons, saturated ketones, ester derivatives of ethyl and diethyleneglycol, alkylphosphoric acids, alkylcarboxylic acids, and alkylamines.

U.S. Pat. No. 3,033,864 discloses a process for recovering alkanolamines from mixtures containing hetrocyclic nitrogen compounds such as piperazines by azeotropic distillation. In the process, the mixture of pyrazine or piperazine and alkanolamines were fractionally distilled with a codistillation agent whereby the lower boiling azeotrope of the codistillation agent and alkanolamine were separated as distillates and the residue or bottoms enriched with respect to pyrazine and piperazine. Representative codistillation agents included aliphatic hydrocarbons, aromatic hydrocarbons and nuclear chlorinated aromatic hydrocarbons.

SUMMARY OF THE INVENTION

This invention relates to an improved process for the separation of methoxyisopropylamine (MOIPA) from a methoxyisopropylamine-water azeotrope. In the process the methoxyisopropylamine-water azeotrope is contacted with a sufficient amount of diisopropylamine(DIPA) to form a DIPA-water azeotrope which is lower boiling than methoxyisopropylamine. The DIPA-water azeotrope is distilled from the methoxyisopropylamine and recovered as an overhead. The diisopropylamine is separated from the water by decanting followed by the recovery of diisopropylamine in the aqueous phase by distillation.

An advantage of the process described herein is that methoxyisopropylamine can be obtained in essentially anhydrous state without undue processing.

DRAWING

The drawing is a block flow diagram of a process for producing methoxyisopropylamine by the reaction of methoxyisopropanol and ammonia including the distillation train for recovery of methoxyisopropylamine from the reaction product.

DETAILED DESCRIPTION OF THE INVENTION

Referring to the drawing, methoxyisopropanol, e.g., 1-methoxy-2-propanol, and ammonia are reacted in reactor 2 which is a fixed bed catalytic reactor containing a conventional catalyst for effecting amination of the alcohol under amination conditions. Typically these aminations will require a pressure of 200 to 300 psig and a reaction temperature of 150° to 230° C. A nickel or cobalt catalyst is often used as the catalyst and hydrogen is added to maintain the catalyst in an active state. The reaction product is removed from reactor 2 via line 4 and it comprises a mixture of methoxyisopropylamine, unreacted methoxyisopropanol, ammonia, methanol, isopropylamine, water, and impurities. The reaction product is removed via line 4 wherein it is charged to ammonia column 6 for removal of ammonia. Ammonia column 6 is operated at a pressure from about 10 to 30 atmospheres and ammonia is removed as an overhead which then can be treated or recycled to the reaction zone.

The bottoms fraction from ammonia column 6 is removed via line 10 and charged to impurities column 12 for removal of low boiling impurities. The low boiling impurities such as methanol and isopropylamine are removed at this point as they can interfere with the separation of water from a methoxyisopropylamine-water azeotrope. Impurities distillation column 12 is operated at pressure ranging from about 20 to 100 psig, although pressure is not a critical parameter in this operation. The low boiling product comprising methanol and methylisopropylamine is removed via line 14. A bottoms product which comprises the unreacted methoxyisopropanol, methoxyisopropylamine, and water is removed from impurities column 12 via line 16 wherein it is charged to water removal column 18. Diisopropylamine is added to column 18 via line 20 in sufficient amount to form a diisopropylamine-water azeotrope. Typically, this will range from about 150 to 170 parts by weight of diisopropylamine per 100 weight parts of the methoxyisopropylamine amine-water azeotrope. The essential requirement is that sufficient diisopropylamine is added as makeup to water removal column 18 to maintain sufficient inventory to remove essentially all of the water. Diisopropylamine is inert to methoxyisopropylamine and forms a lower boiling azeotrope with water which can be easily separated from the methoxyisopropylamine-water azeotrope. Operation of water removal column 18 is conducted at pressures ranging from about 100 to 150 psig. A bottoms product is removed from water removal column 18 via line 22 and contains methoxyisopropylamine, unreacted methoxyisopropanol and trace impurities. This bottoms fraction then is separated in methoxyisopropylamine purification column 26 with methoxyisopropylamine being recovered as an overhead and the bottoms which contain unreacted methoxyisopropanol and the trace impurities are removed via line 28 and recycled back to reactor 2. Often a purge stream is taken from line 28 to remove unwanted trace impurities as the concentration of these impurities builds in the system.

The diisopropylamine-water azeotrope is removed as an overhead from the water removal column 18 via line 24 wherein it is charged to a decanter 32. Diisopropylamine is immiscible in water and generates an organic phase as a top layer. This top layer can be recycled via line 34 to water removal column 18. A bottoms comprising diisopropylamine and water with the concentration of diisopropylamine being about 1 to 3% by weight is removed via line 36 wherein it is charged to diisopropylamine column 38. In diisopropylamine column 38, diisopropylamine is distilled from the water with the water-diisopropylamine azeotrope being recovered as an overhead via line 40 and water being removed via line 42.

The following examples are provided to illustrate various embodiments of the invention and are not intended to restrict the scope thereof.

EXAMPLE 1

A 6 inch diameter batch distillation column was packed with 24 feet of a Koch Sulzer packing was pressurized to 100 psig. Diisopropylamine was used as the entraining agent and a feed of 156 weight parts diisopropylamine per 100 weight parts of methoxyisopropylamine-water azeotrope was used. The column was operated as a continuous column with the overhead being charged to a decanter. Water, which was the bottom layer in the decanter, was removed and charged to another distillation column for removal of the residual DIPA therefrom in the water layer.

Table 1 below sets forth the composition in percent by weight of the upper layer and lower layer in the decanter as well as the composition of the still bottoms in water removal Column 18.

TABLE 1

| Component | Decanter Upper Layer | Decanter H$_2$O Layer | Column (18 bottoms) |
|---|---|---|---|
| H$_2$O | 4.5 | 90.9 | 0.01 |
| DIPA | 92.3 | 5.6 | 1.1 |
| MOIPA | 1.4 | 0.01 | 68.5 |
| MOIPOH | — | 0.2 | 30.2 |
| Others | 1.8 | 3.2 | 0.1 |

DIPA refers to diisopropylamine
MOIPA refers to methoxyisopropylamine
MOIPOH refers to methoxyisopropanol At this stage in the process it is clear that DIPA is viable as a codistillation agent since there is essentially no water in the bottoms fraction of water removal Column 18.

EXAMPLE 2

Purification of Moipa

Distillation bottoms from water removal column 18 from Example 1 was charged to an 8 inch diameter ammonia column packed with 27 feet of a Koch-Sulzer packing. The column was operated at a pressure ranging from about 8 to 12 psig and a reflux ratio of greater than 10:1 was used because of a control problem associated with the column.

Table 2 sets forth a typical composition in percent by weight of the overheads and bottoms from the methoxyisopropylamine purification column.

TABLE 2

| | Water Removal Column 26 | |
|---|---|---|
| Component | Overhead | Bottoms |
| Water | 0.1 | <0.1 |
| MOIPA | 99.8 | 4.6 |
| MOIPOH | <0.1 | 94.6 |
| Others | 0.1 | 0.8 |

These data show that essentially anhydrous methoxyisopropylamine is produced as an overhead. Further, there is little to no contamination of the methoxyisopropylamine product.

EXAMPLE 3

The procedure of Example 1 was repeated except that cyclohexane was substituted for diisopropylamine. Table 3 sets forth the comparative results.

TABLE 3

| Component | Decanter Upper Layer | Decanter H$_2$O Layer | Column (18 bottoms) |
|---|---|---|---|
| H$_2$O | 0.7 | 28.0 | 2.0 |
| Cyclohexane | 97.2 | 1.2 | 1.1 |
| MOIPA | 2.1 | 66.8 | 68.5 |
| MOIPOH | — | 4.0 | 30.2 |
| Others | 1.8 | 3.2 | 1.7 |

These data show that using cyclohexane as a water entrainer also carries MOIPA to the water layer in the decanter 32 and prevents the recovery of all the MOIPA produced in reactor 2. Although not shown by the data, visual inspection of the decanter during operation often showed that a single phase was present and no water removal occurred.

EXAMPLE 4

Analyses were taken of each overhead and bottoms for each column. Tables 5-9 set forth typical compositions in percent by weight obtained from each column.

TABLE 5

NH₃ Column 6

| Component | Overhead | Bottoms |
|---|---|---|
| Ammonia | 99.9 | 0.1 |
| Water | 0.1 | |
| MOIPA | | |
| MOIPOH | | |
| Others | | |

TABLE 12

Impurities Columns 6

| Component | Overhead | Bottoms |
|---|---|---|
| Water | 2.3 | 11.5 |
| MeOH | 12.8 | <0.1 |
| MIPA | 76.7 | <0.1 |
| MOIPA | 4.9 | 60.2 |
| MOIPOH | | 28.2 |
| Others | 3.3 | 0.1 |

TABLE 7

Water Removal Column 18

| Component | Decanter Bottoms | Bottoms |
|---|---|---|
| Water | 90.9 | <0.1 |
| MOIPA | <0.1 | 68.0 |
| MOIPOH | 0.2 | 31.5 |
| DIPA | 5.6 | 0.4 |
| Others | 3.2 | <.1 |

TABLE 8

Methoxyisopropylamine Purification Column 26

| Component | Overhead | Bottoms |
|---|---|---|
| Water | 0.1 | <0.1 |
| MOIPA | 99.8 | 4.6 |
| MOIPOH | <0.1 | 94.6 |
| Others | 0.1 | 0.8 |

TABLE 9

DIPA Column 38

| Component | Overhead | Bottoms |
|---|---|---|
| Water | 28.0 | 99.8 |
| TOC | | 1000-10,000 ppm |
| DIPA | 62.8 | |
| Others | 10.0 | |

TOC refers to total organic carbon in ppm.

What is claimed is:

1. In a process for the separation and recovery of an amine from an amine-water azeotrope wherein the azeotrope is contacted with a codistillation agent for forming a low boiling codistillation agent-water azeotrope and then the codistillation agent-water azeotrope is distilled from the amine, the improvement for effecting separation and recovery of methoxyisopropylamine from a methoxyisopropylamine-water azeotrope which comprises contracting the methoxyisopropylamine-water azeotrope with a codistillation agent consisting essentially of diisopropylamine.

2. The process of claim 1 wherein diisopropylamine is added to the methoxyisopropylamine-water azeotrope in amount from about 150 to 170 weight parts per 100 weight parts of methoxyisopropylamine-water azeotrope.

3. In a process for the preparation of a purified methoxyisopropylamine product wherein methoxyisopropanol is reacted with ammonia under amination conditions to form a crude methoxyisopropylamine in water reaction product and the methoxyisopropylamine recovered therefrom, the improvement for obtaining essentially anhydrous methoxyisopropylamine which comprises:

a) distilling unreacted ammonia from said crude reaction product; and obtaining a crude methoxyisopropylamine;

b) distilling low boiling impurities from said crude methoxyisopropylamine and removing an azeotrope of methoxyisopropylamine in water;

c) contacting the azeotrope of methoxyisopropylamine and water with diisopropylamine in sufficient proportion to form a diisopropylamine-water azeotrope;

d) distilling said azeotrope of diisopropylamine in water from the azeotrope of methoxyisopropylamine in water and recovering an overhead essentially free of methoxyisopropylamine and a bottoms containing methoxyisopropylamine and essentially free of water;

e) decanting the overhead of liquid diisopropylamine as an upper organic layer and a lower aqueous layer essentially free of diisopropylamine and, f) distilling the bottoms obtained from step (d) and obtaining an essentially purified methoxyisopropylamine product.

* * * * *